United States Patent
Jahaniaval

(10) Patent No.: US 7,645,467 B2
(45) Date of Patent: Jan. 12, 2010

(54) PROCESS FOR PREPARING A FOOD GRADE PLANT JELLY WITH NO PETROLEUM OR ANIMAL BASED PRODUCTS

(76) Inventor: Firouz Jahaniaval, 71 Procter Avenue, Thornhill, Ontario (CA) L3T 1M6

( * ) Notice: Subject to any disclaimer, the term of this patent is extended or adjusted under 35 U.S.C. 154(b) by 351 days.

(21) Appl. No.: 11/416,182

(22) Filed: May 3, 2006

(65) Prior Publication Data

US 2006/0257353 A1 Nov. 16, 2006

Related U.S. Application Data

(60) Provisional application No. 60/676,961, filed on May 3, 2005.

(51) Int. Cl.
*A61K 36/48* (2006.01)

(52) U.S. Cl. .................................................. 424/757

(58) Field of Classification Search ............... None
See application file for complete search history.

(56) References Cited

U.S. PATENT DOCUMENTS

| 127,568 | A | | 6/1872 | Chesbrough |
| 4,497,158 | A | * | 2/1985 | Durr et al. .................... 53/428 |
| 4,784,849 | A | | 11/1988 | Tutsky |
| 5,069,915 | A | * | 12/1991 | Devitt et al. ................ 426/93 |
| 5,310,556 | A | * | 5/1994 | Ziegler ....................... 424/401 |
| 5,407,678 | A | | 4/1995 | Rose et al. |
| 5,756,142 | A | * | 5/1998 | Reckweg et al. ............ 426/603 |
| 5,869,061 | A | | 2/1999 | Brug |
| 5,932,230 | A | | 8/1999 | DeGrate |
| 6,660,776 | B1 | | 12/2003 | McDaniels, III |
| 6,780,439 | B2 | | 8/2004 | Wilk |
| 2003/0161935 | A1 | * | 8/2003 | Kakuda et al. ............. 426/604 |
| 2005/0053635 | A1 | | 3/2005 | Puglia |
| 2006/0188618 | A1 | * | 8/2006 | Van De Sype et al. ... 426/330.6 |

OTHER PUBLICATIONS

Foldvari, M., "Effect of vehicle on topical liposomal drug delivery: petrolatum bases.", J. Microencapsul, 1996, vol. 13, No. 5, pp. 589-600.

Fiume, Z., "Final report on the safety assessment of Lecithin and Hydrogenated Lecithin.", Int. J. Toxicol., 2001, vol. 20, Suppl. 1, pp. 21-45.

* cited by examiner

*Primary Examiner*—Christopher Tate
*Assistant Examiner*—Deborah A. Davis
(74) *Attorney, Agent, or Firm*—Bereskin and Parr LLP/S.E.N.C.R.L., s.r.l.; Patricia Polkins

(57) ABSTRACT

The present invention provides a method for the preparation of a plant jelly in the form of a jelly-like product wherein selected phospholipids (for example, PC, PE and lyso-PC/PE) play an important role in jellifying the mixture. The plant jelly has a plant hard fat blend and an oil blend in which the plant hard fat blend is made up of about 10-20% of a fat with a melting point of 30-40° C. and about 4-10% of a vegetable fat, and in which the oil blend is made up of about 1-3.5% phospholipids and about 70-80% liquid oil.

24 Claims, No Drawings

PROCESS FOR PREPARING A FOOD GRADE PLANT JELLY WITH NO PETROLEUM OR ANIMAL BASED PRODUCTS

This application claims the benefit under 35 USC § 119(e) from U.S. provisional patent application Ser. No. 60/676,961, filed May 3, 2005.

FIELD OF THE INVENTION

The present invention is in the field of food grade materials, particularly in the preparation of healthy, food grade, non-animal or petroleum base products and value added plant jelly.

BACKGROUND OF THE INVENTION

In the past, ointments, lubricants and skin care products have been prepared from a colorless to amber hydrocarbon mixture which is obtained from oil wells and/or by fractional distillation of petroleum, also known as petroleum jelly—a semisolid and jelly-like material (Chesebrough, U.S. Pat. No. 127,568). Other cosmetic uses of petroleum include petroleum pomade for the hair, which makes use of the finest grade of petroleum jelly, and glycerin cream for chapped hands. Due to the non reactive, oily nature and semisolid characteristics of petroleum jelly and the medium melting range of the hydrocarbon chain, petroleum has been widely used in skin care and non cosmetic applications.

Similar products having a petroleum jelly-like property have also been available for use in both cosmetic and non cosmetic applications. These products are typically prepared from 10-30% beeswax and 70-90% liquid paraffin (a mineral oil), in which the mineral oil is jellified by the beeswax.

Apart from being prepared from petroleum, skin care products prepared from vegetable oils, oleoresins, aromas, waxes and plant extracts have also been developed for healing and caring dry skin with or without zinc. U.S. Pat. No. 6,780,439 (Wilk) discloses a novel solution for the treatment of skin sores and wounds to promote healing and reduce scarring in which the solution consists of cedar leaf oil, zinc oxide ointment, calamine lotion and an ointment base in varying quantities. In another United States Patent Application No. 20050053635 (Puglia et al.), a vehicle containing refined peanut oil for topical use in skin care and for use in skin care therapeutics, a process for making the vehicle and a composition and therapeutic composition made from that process was disclosed.

Although in some instances, olive oil, coconut oil and cocoa butter have been used as a main or second ingredient and or in combination with butter oil and other animal fats to cure or rub dry skins, products having petroleum jelly characteristic with 100% vegetable oil and vegetable oil derivatives have not been reported.

Therefore, there remains a need to provide a plant jelly with 100% vegetable oil and vegetable oil derivatives and no petroleum or animal based products.

SUMMARY OF THE INVENTION

The present invention relates to a method to produce a plant jelly with food grade purity. The plant jelly of the present invention may be used as a rubbing jelly or lubricant for the skin, particularly normal or dry skin, or as a lubricant for food processing machines where food grade materials are needed. In this plant jelly, certain phospholipids (for example, phosphotidylcholine (PC), phosphotidylethanolamine (PE), lyso-phosphatidylcholine (lyso-PC) and/or lyso-phosphatidylethanolamine (lyso-PE)) are used to increase the oil binding capacity and the wetability of the oil/fat blend as well as the health benefit of the phospholipids for skin. The total fat content of this plant jelly comprises about 10-20% of a fat with a melting point of 30-40° C. and about 4-10% vegetable fat, about 1-3.5% phospholipids and about 70-80% liquid oil. Particularly, the total fat content of this plant jelly comprises about 13-20% of a fat with a melting point of 30-35° C. and about 4-8% vegetable fat, about 2-3.5% phospholipids and about 70-80% liquid oil. This provides a plant jelly having a final composition of 100% vegetable oil/fat blend.

Accordingly, the present invention includes a method for preparing a plant jelly comprising:

(a) combining a plant hard fat blend comprising about 10-20% of a fat with a melting point of 30-40° C. and about 4-10% of vegetable fat with an oil blend comprising about 1-3.5% phospholipids and about 70-80% liquid oil; and (b) treating the plant hard fat blend and the oil blend under conditions to produce the plant jelly.

In an embodiment of the invention, the method for preparing a plant jelly comprises:

(a) combining a plant hard fat blend comprising about 13-20% of a fat with a melting point of 30-35° C. and about 4-8% of vegetable fat with an oil blend comprising about 2-3.5% phospholipids and about 70-80% liquid oil; and (b) treating the plant hard fat blend and the oil blend under conditions to produce the plant jelly.

The present invention also relates to a plant jelly comprising a plant hard fat blend comprising about 10-20% of a fat with a melting point of 30-40° C. and about 4-10% of vegetable fat, an oil blend comprising about 1-3.5% phospholipids and about 70-80% liquid oil, prepared using the method of the present invention. More particularly, the present invention relates to a plant jelly comprising a plant hard fat blend comprising about 13-20% of a fat with a melting point of 30-35° C. and about 4-8% of vegetable fat, an oil blend comprising about 2-3.5% phospholipids and about 70-80% liquid oil, prepared using the method of the present invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

A simple and economical method to produce a plant jelly with 100% vegetable oil and vegetable oil derivatives has been developed. The total fat content in the plant jelly prepared using this method comprises a plant hard fat blend comprising about 10-20% of a fat with a melting point of 30-40° C. and about 4-10% of vegetable fat, and an oil blend comprising about 1-3.5% phospholipids and about 70-80% liquid oil. Particularly, the total fat content of this plant jelly comprises about 13-20% of a fat with a melting point of 30-35° C. and about 4-8% vegetable fat, about 2-3.5% phospholipids and about 70-80% liquid oil. This provides a plant jelly having a final composition made up of 100% vegetable oil/fat blend.

Accordingly, the present invention includes a method for preparing a plant jelly comprising:

(a) combining a plant hard fat blend comprising about 10-20% of a fat with a melting point of 30-40° C. and about 4-10% of vegetable fat with an oil blend comprising about 1-3.5% phospholipids and about 70-80% liquid oil; and (b) treating the plant hard fat blend and the oil blend under conditions to produce the plant jelly.

In an embodiment of the invention, the method for preparing a plant jelly comprising:

(a) combining a plant hard fat blend comprising about 13-20% of a fat with a melting point of 30-35° C. and about 4-8% of vegetable fat with an oil blend comprising about 2-3.5% phospholipids and about 70-80% liquid oil; and (b) treating the plant hard fat blend and the oil blend under conditions to produce the plant jelly.

As used herein, the term "plant jelly" is understood to mean a mixture of vegetable oils and fats containing different triglycerides and phospholipids which is in jelly form at room temperature of about 22° C. The term "extra virgin olive oil" refers to olive oil extracted from olive fruit by the cold press method so as to maintain its distinguished color and flavor. The olive oil may comprise about 70-80% of the plant jelly. The term "cocoa butter" as used herein refers to a cocoa fat comprising at least about 10-20% of a fractionated or extracted fat from cocoa bean and wherein the total level of palmitic (P), stearic (S) and oleic (O) acids present is 30-33% each. Cocoa butter fats will be solid at temperatures below about 35° C. The term "vegetable fats" as used herein refers specifically to the hard fat obtained from fractionation of the tropical oils such as palm and coconut oils and or fully hydrogenated of the cottonseed oil. The vegetable fats are added to the mixture of olive oil, cocoa butter and phospholipids to produce a suitable plant jelly with the desire hardness and texture.

Phospholipids that are suitable for use in the method of the present invention include those which can stabilize a plant jelly. In an embodiment of the invention, the phospholipid is one that interacts, for example by binding, to both fat crystals and liquid oil. Examples of phospholipids that may be used in the method of the invention include, but are not limited to, one or more of phosphotidylcholine (PC), phosphotidylethanolamine (PE), lyso-phosphatidylcholine (lyso-PC) and lyso-phosphatidylethanolamine (lyso-PE). In an embodiment of the invention, the phospholipids comprise a mixture of PC, PE, lyso-PC and lyso-PE. In a further embodiment of the invention, the ratio of PC:PE (including lyso-PC/lyso-PE) ranges from about 35:65 to about 70:30, suitably about 50:50.

The term "lubricant" as used herein in reference to the application of the plant jelly of the present invention means a lubricant for use on normal or dry skin and also for use in food processing machines, where food grade materials are needed.

In an embodiment of the invention, the liquid oil may be selected from any suitable non-hydrogenated oil which is a liquid at temperatures greater than about 5° C. Examples of such oils include, but are not limited to, olive oil, palm oil, fish oil, flaxseed oil, canola oil, sunflower oil, safflower oil, soybean oil, cotton oil, corn oil, and peanut oil. In an embodiment of the invention, the liquid oil is olive oil. Since olive oil has a significantly higher amount of squalene than other seed oils, and thus providing a lower ratio of oxidation rate when compared to other oils, olive oil has been linked to numerous health benefits.

In an embodiment of the invention, the plant hard fat blend comprises about 10-20%, suitably 13-20%, of a fat with a melting point of 30-40° C., suitably 30-35° C., in which the fat is selected from one or more of cocoa butter, cocoa fat, intermediate melting point triglycerides (IMP triglycerides) such as interesterified fat, cocoa butter substitute and any fractionated tropical and non-tropical fat with such a melting point. More particularly, the cocoa butter includes a combination of POP, POS and SOS in which P, O and S represent palmitic, stearic and oleic acids respectively in the form of triglycerides with intermediate melting point of 30-40° C., suitably 30-35° C.

In another embodiment of the invention, the vegetable fat is selected from any suitable fat which is a solid at temperatures below about 40-55° C. Examples of such fats include, but are not limited to, palm stearin, cotton stearin, corn stearin and canola stearin or mixtures thereof.

In an embodiment of the invention, the plant hard fat blend is a mixture comprising cotton stearin and palm stearin. In a further embodiment of the invention, the plant hard fat blend is a mixture of cotton stearin and palm stearin with no trans fat.

Other additives, typically used in the preparation of comestible lubricant, may also be added to the plant jelly product. Such additives include, but are not limited to, coloring agents, odorants, healing agents and preservatives.

All percentages used herein refer to a percentage of the weight of a specified mixture, component of the plant jelly or the plant jelly itself.

The jellification effect of the phospholipids, with a plant hard fat blend which is made up of about 10-20% of a fat with a melting point of 30-40° C., suitably about 13-20% a fat with a melting point of 30-35° C., and about 4-10%, suitably about 4-8% of vegetable fat, and an oil blend, which is made up of about 70-80% liquid oil and about 1-3.5%, suitably about 2-3.5% phospholipids, is based on the use of phospholipids and fat crystals, and blending the phospholipids and vegetable fats using the appropriate type and ratio and temperature. Because the jelling characteristic is required, the method involves the use of certain phospholipids to stabilize the system. By using about 1-3.5%, suitably about 2-3.5% phospholipids (for example, PC, PE and/or lyso-PC/lyso-PE), about 4-10%, suitably about 4-8% vegetable fats (for example, stearins), about 10-20% of a fat with a melting point of 30-40° C., suitably about 13-20% of a fat with a melting point of 30-35° C. (for example, cocoa butter or any suitable intermediate melting point triglycerides) and about 70-80% liquid oil (for example, olive oil), the fat/oil blend mixture can be formed into a jelly-like structure in the plant jelly.

In an embodiment of the invention, the plant jelly comprises (as a percentage by weight of the oil and fat only) about 70-80%, suitably about 77%, by weight of liquid oil such as olive oil, about 1-3.5%, suitably about 2%, by weight of one or more phospholipids, about 10-20% of a fat with a melting point of 30-40° C., suitably about 12% of a fat with a melting point of 30-35° C. such as cocoa butter, and about 4-10%, suitably about 9% by weight of vegetable fat.

In another embodiment of the invention, the plant jelly comprises (as a percentage by weight of the oil and fat only) about 70-80%, suitably about 74.2%, by weight of liquid oil such as olive oil, about 1-3.5%, suitably about 3.2%, by weight of one or more phospholipids, about 10-20% of a fat with a melting point of 30-40° C., suitably about 16% of a fat with a melting point of 30-35° C. such as cocoa butter, and about 4-10%, suitably about 6.6% by weight of vegetable fat such as stearin.

The plant jelly can be prepared by simply dissolving the fat with a melting point of 30-40° C. and the vegetable fat in a mixture of liquid oil and phospholipids in any order, with thorough mixing and warming.

In an embodiment of the invention, the plant jelly comprises (as a percentage by weight of the fat only) about 70-80%, suitably about 77%, by weight of liquid oil such as olive oil, about 1-3.5%, suitably about 2%, by weight of phospholipids, about 10-20% of a fat with a melting point of 30-40° C., suitably about 12% of a fat with a melting point of 30-35° C. such as cocoa butter, and about 4-10%, suitably about 9% by weight of vegetable fat.

In an alternative embodiment of the invention, the plant jelly may comprise (expressed as a percentage by weight of the fat only) about 70-80%, suitably about 74.2%, by weight of liquid oil, such as olive oil, about 10-20%, suitably about 16%, by weight of a fat with a melting point of 30-40° C., suitably with a melting point of 30-35° C., such as cocoa butter, about 4-10% of a vegetable fat, suitably about 6.6% such as stearins and about 1-3.5% of phospholipids, suitably about 3.2% such as fractionated soy lecithin.

The plant jelly may be prepared, for example, by warming the oil and fat mixture to a temperature in the range of 40° C. to 60° C. (while not exceeding 60° C.), suitably at about 45° C.-55° C., adding, in any order of a fat with a melting point of 30-40° C. and vegetable fat into the liquid oil and phospholipids until everything is dissolved.

To prepare the plant jelly, the oil and fat are suitably mixed and warmed gradually with mixing.

To prepare the plant jelly, the fat is suitably added to the warmed liquid oil gradually with mixing. The mixing speed can be any range depending upon the container and the volume of the oil/fat mixture. The optimum range for mixing is 30-35 rpm. A person skilled in the art would be able to determine the proper addition rates, mixing speeds, mixing shears for a particular volume of material by adjusting the addition rates, mixing speeds and shear forces during the addition of the fat with a melting point of 30-40° C. and vegetable fat into the liquid oil and phospholipids.

Once suitably combined, the mixture can be cooled using, for example, a heat exchanger. Cooling may be achieved using any suitable method, such as using a "heat exchanger" at a set temperature of about 0° C. to 5° C. or holding at cool storage with temperature of not more than 15° C. for crystallization. Cooling temperature is not crucial for this product, but needs to be cooled less than 15° C. in order to crystallize the fat in the liquid oil for forming the jelly-like structure. While not wishing to be limited by theory, it is believed that cooling or supercooling crystallizes the fat with a melting point of 30-40° C. and vegetable fat by interaction of phospholipids with fat and oil and produces a jellify mixture within an expanded phospholipids-fat crystal network.

In embodiments of the present invention, the plant jelly is prepared by combining the fat with a melting point of 30-40° C. and vegetable fat and phospholipids and liquid oil mixture with blending at a temperature above the crystallization point of the vegetable fat, to provide a mixture of oil, fat and phospholipids. In a further embodiment involving the direct use of a fat with a melting point of 30-40° C., vegetable fat and phospholipids in the plant jelly at a production level, both fats and phospholipids are added into the liquid oil and mixed under heat (about 55-60° C.) to produce the plant jelly mix. The plant jelly mix then can be cooled below the oil and fat mixture melting point to produce the plant jelly.

In processing of the plant jelly, the liquid oil is typically blended with the fat with a melting point of 30-40° C. and vegetable fat at a temperature about 55-60° C., followed by cooling or super-cooling with or without the heat exchanger (Votator or Perfector) to obtain the jellified product.

In another aspect of the present invention there is provided a method for the preparation of a plant jelly wherein the total fat content of the plant jelly comprises a maximum of about 70-80% liquid oil, a minimum of about 10-20% of a fat with a melting point of 30-40° C., a maximum of about 4-10% vegetable fat and about 1-3.5% phospholipids, comprising:

(I) preparing an oil blend and a plant hard fat blend comprising:
  (a) combining the liquid oil with one or more phospholipids to prepare the oil blend;
  (b) combining one or more vegetable fats and a fat with a melting point of 30-40° C. to prepare a plant hard fat blend; and
  (c) combining (a) and (b) at a temperature above the crystallization temperature of the fat;
(II) mixing the oil blend and the plant hard fats blend and warming the mixture until the plant hard fat blend dissolves in the oil blend, with continuous blending; and
(III) cooling the mixed oil blend and plant hard fat blend at a temperature below the melting temperature of the vegetable fat until a plant jelly is obtained.

In an embodiment of the present invention, there is provided a method for the preparation of a plant jelly wherein the total fat content of the plant jelly comprises a maximum of about 70-80% liquid oil, a minimum of about 13-20% of a fat with a melting point of 30-35° C., a maximum of about 4-8% vegetable fat and about 2-3.5% phospholipids, comprising:

(I) preparing an oil blend and a plant hard fat blend comprising:
  (a) combining the liquid oil with one or more phospholipids to prepare the oil blend;
  (b) combining one or more vegetable fats and a fat with a melting point of 30-35° C. to prepare a plant hard fat blend; and
  (c) combining (a) and (b) at a temperature above the crystallization temperature of the fat;
(II) mixing the oil blend and the plant hard fat blend and warming the mixture until the plant hard fat blend dissolves in the oil blend, with continuous blending; and
(III) cooling the mixed oil blend and plant hard fat blend at a temperature below the melting temperature of the vegetable fat until a plant jelly is obtained.

In another aspect of the present invention, there is provided a plant jelly wherein the total fat content of the plant jelly comprises a maximum of about 70-80% liquid oil, a minimum of about 10-20% of a fat with a melting point of 30-40° C., suitably about 13-20% of a fat with a melting point of 30-35° C., a maximum of about 4-10% vegetable fat, suitably about 4-8% vegetable fat, and about 1-3.5% phospholipids, suitably about 2-3.5% phospholipids.

In an embodiment of the present invention, there is also provided a plant jelly wherein the total fat content of the plant jelly comprises about 77% liquid oil, about 12% of a fat with a melting point of 30-35° C., about 9% vegetable fat and about 2% phospholipids, the plant jelly being prepared using a method as described herein.

In another embodiment of the present invention, there is also provided a plant jelly wherein the total fat content of the plant jelly comprises a minimum of about 74.2% liquid oil, a maximum of about 16% of a fat with a melting point of 30-35° C., a maximum of about 6.6% vegetable fat and about 3.2% phospholipids, the plant jelly being prepared using a method as described herein.

The following non-limiting examples are illustrative of the invention:

EXPERIMENTAL EXAMPLES

Example 1

Extraction of Ethanol or Isopropanol and/or Acetone Soluble Fractions of Soy Lecithin Solvents such as ethanol and isopropanol were used to extract PC, PE, lyso-PC and lyso-PE from soy lecithin under non-heat or heat treatment conditions. The 5:1 ratio of solvent and soy lecithin (solvent:lecithin ratio can be varied between 2:1 to 10:1) was mixed in a beaker and stirred thoroughly with high shear agitator to produce small particles of lecithin-in-solvent mixture. Mixing time is dependent upon the amount of solvent-lecithin mixture and the shear rates. The mixture creates two immiscible phases after stopping agitation and sitting the mixture at room temperature: 1) upper phase-containing solvent and phospholipids (PC, lyso-PC and PE) and small amount of other phospholipids; 2) lower phase-containing soy lecithin with lower amount of PC, lyso-PC, PE and materials which did not dissolve in ethanol or isopropanol such as soybean oil. The upper phase was decanted and evaporated to remove ethanol or isopropanol from the mixture and the residual was collected as enriched PC, PE and lyso-PC-PE. In similar procedure acetone was used to extract lyso-PC-PE and soybean oil from soy lecithin using the same ratio of solvent and lecithin. Practically acetone does not dissolve some phospholipids especially, phosphatidylinositol (PI), phosphotidylserine (PS) and phosphatidylcholine (PC). The acetone soluble fraction of lecithin was decanted and evaporated to extract the soybean oil, lyso-PC and PE. The extracted acetone soluble fraction of lecithin was mixed with PC obtained from the market or by extraction from lecithin to produce PC, lyso-pC-PE and PE mixture. The amount of PC and lyso-PC/PE comprises between 20:80 to 70:30% (PC:lyso-PC/PE) in each extraction or combination.

Example 2

Procedure for Making Plant Jelly

The fat fraction in plant jelly is produced by adding ethanol and/or isopropanol soluble fractions of soy lecithin into the olive oil and mixing with both cocoa butter and stearins such as canola, cotton, soy, palm stearins and/or intermediate melting point triglycerides (IMP triglycerides) such as interesterified fats, cocoa butter substitutes having SOS, POS and POP composition in their triglyceride backbone using heat to dissolve ethanol and isopropanol fractions of lecithin in olive oil and cocoa butter and stearin. The mixture was heated up to 60° C. to dissolve stearins in olive oil. The melted mixture was then cooled to produce plant jelly.

Example 3

Representative Formulation

| Ingredient | Plant Jelly (%)* |
|---|---|
| liquid Oil (extra virgin olive) | 74.2 |
| Phospholipids (PC, lyso-PC-PE) | 3.2 |
| Cocoa butter | 16 |
| Vegetable fat (Cotton, canola and palm Stearin) | 6.6 |

*percent by weight of the final mixture

Processing Procedures (Using Above Ratios):

Plant Jelly

Plant jelly was prepared by warming olive oil and phospholipids mixture and adding cocoa butter and vegetable fats. The cocoa butter and vegetable fats were completely dissolved in olive oil by thoroughly mixing with a medium shear rate mixer. A plant jelly mixture was prepared by adding phospholipids and dissolving stearin and cocoa butter in extra virgin olive oil with the medium shear rate mixer having a mixing speed rate of about 30-35 rpm. Other rates and blending speed may be preferred under other conditions, for example, when using different volume.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

I claim:

1. A method of preparing a food grade plant jelly comprising:
   (a) combining a plant hard fat blend with an oil blend;
   (b) warming the combination in (a) and mixing until the plant hard fat blend dissolves in the oil blend;
   (c) cooling the combined plant hard fat blend and oil blend to a temperature below the melting temperature of the vegetable fat and mixing until a plant jelly is obtained,
   wherein the plant hard fat blend comprises, as a percentage by weight of the plant jelly, about 10-20% of a fat with a melting point of 30-40° C. and about 4-10% of a vegetable fat, and the oil blend comprises, as a percentage by weight of the plant jelly, about 1-3.5% phospholipids and about 70-80% liquid oil, and wherein the phospholipids are ethanol and/or isopropanol soluble phospholipids from soy lethicin.

2. The method according to claim 1, wherein the plant hard fat blend comprises, as a percentage by weight of the plant jelly, about 13-20% of a fat with a melting point of 30-35° C., and about 4-10% of vegetable fat.

3. The method according to claim 2, wherein the fat with the melting point of 30-35° C. is selected from one or more of cocoa butter, cocoa fat, intermediate melting point triglyceride (IMP triglycerides), interesterified fat, cocoa butter substitute and any suitable fractionated tropical and non-tropical fat.

4. The method according to claim 3, wherein the cocoa butter includes a combination of POP, POS and SOS in which P, O and S represent palmitic, oleic and stearic acids respectively, in the form of triglycerides with an intermediate melting point of 30-35° C.

5. The method according to claim 1, wherein the phospholipids in the oil blend are present in an amount, as a percentage by weight of the plant jelly, of about 2-3.5%.

6. The method according to claim 1, wherein the one or more phospholipids are selected from one or more of phosphotidylcholine (PC), phosphotidylethanolamine (PE), lyso-phosphatidylcholine (lyso-PC) and lyso-phosphatidylethanolamine (lyso-PE).

7. The method according to claim 6, wherein the phospholipids comprise a mixture of PC, PE, lyso-PC and lyso-PE.

8. The method according to claim 7, wherein the ratio of PC:PE/lysoPC/lysoPE is from about 35:65 to about 70:30.

9. The method according to claim 8, wherein the ratio of PC:PE/lysoPC/lysoPE is 50:50.

10. The method according to claim 1, wherein the liquid oil is any suitable non-hydrogenated oil which is a liquid at temperatures greater than about 5° C.

11. The method according to claim 1, wherein the liquid oil is selected from one or more of olive oil, palm oil, fish oil, flaxseed oil, canola oil, sunflower oil, safflower oil, soybean oil, cotton oil, corn oil and peanut oil.

12. The method according to claim 11, wherein the liquid oil is olive oil.

13. The method according to claim 1, wherein the vegetable fat in the plant hard fat blend is present, as a percentage by weight of the plant jelly, in an amount of about 4-8%.

14. The method according to claim 1, wherein the vegetable fat is selected from one or more of palm stearin, cotton stearin, corn stearin, canola stearin and any suitable vegetable fat with a melting point of about 40-55° C.

15. The method according to claim 14, wherein the vegetable fat is a mixture of cotton stearin and palm stearin.

16. The method according to claim 14, wherein the vegetable fat is a mixture of cotton stearin and palm stearin with no trans fat.

17. The method according to claim 1, further comprising combining the plant hard fat blend and the oil blend with other additives, used in the preparation of comestible spreads, to the plant jelly.

18. The method according to claim 17, wherein the additives are selected from one or more of coloring agents, odorants, healing agents and preservatives.

19. The method according to claim 1, wherein the plant hard fat blend is added to the oil blend.

20. The method according to claim 19, wherein the oil blend is at a temperature of about 40° C. to about 60° C.

21. The method according to claim 20, wherein the oil blend is at a temperature of about 45° C. to about 55° C.

22. The method according to claim 1, wherein the liquid oil is present in an amount of about 77%, the phospholipids are present in an amount of about 2%, the vegetable fat is present in an amount of about 9% and the fat with a melting point of 30-35° C. is present in an amount of about 12%, wherein the amounts are a percentage by weight of the plant jelly.

23. A method for the preparation of a food grade plant jelly wherein the total fat content of the plant jelly comprises, as a percentage by weight of the plant jelly, a maximum of about 70-80% liquid oil, a minimum of about 10-20% of a fat with a melting point of 30-40° C., a maximum of about 4-10% vegetable fat and about 1-3.5% phospholipids, comprising:
(I) preparing an oil blend and a plant hard fat blend comprising:
    (a) combining the liquid oil with one or more phospholipids to prepare the oil blend;
    (b) combining one or more vegetable fats and a fat with a melting point of 30-40° C. to prepare the plant hard fat blend; and
    (c) combining (a) and (b) at a temperature above the crystallization temperature of the fat;
(II) mixing the oil blend and the plant hard fat blend and warming the mixture until the plant hard fat blend dissolves in the oil blend, with continuous blending; and
(III) cooling the mixed oil blend and plant hard fat blend at a temperature below the melting temperature of the vegetable fat until a plant jelly is obtained,
wherein the phospholipids are ethanol and/or isopropanol soluble phospholipids from soy lethicin.

24. The method according to claim 23, wherein the total fat content of the plant jelly comprises, as a percentage by weight of the plant jelly, a maximum of about 70-80% liquid oil, a minimum of about 13-20% of a fat with a melting point of 30-35° C., a maximum of about 4-8% vegetable fat and about 2-3.5% phospholipids.

* * * * *